United States Patent [19]
Cohen

[11] Patent Number: 5,318,526
[45] Date of Patent: Jun. 7, 1994

[54] FLEXIBLE ENDOSCOPE WITH HYPOTUBE ACTIVATING WIRE SUPPORT

[75] Inventor: Donald Cohen, Irvine, Calif.

[73] Assignee: Neuro Navigational Corporation, Costa Mesa, Calif.

[21] Appl. No.: 954,120

[22] Filed: Sep. 29, 1992

[51] Int. Cl.$^5$ .............. A61M 37/00; A61B 1/00; A61B 1/06
[52] U.S. Cl. ............................ 604/95; 128/4; 128/6
[58] Field of Search .......... 604/95, 280, 282; 128/4, 6

[56] References Cited

U.S. PATENT DOCUMENTS

| | | |
|---|---|---|
| 3,253,524 | 5/1966 | Ashizawa et al. .............. 128/4 |
| 3,470,876 | 10/1969 | Barchilon ........................ 604/95 |
| 3,521,620 | 7/1970 | Cook ............................. 128/2.05 |
| 4,329,980 | 5/1982 | Terada ............................ 128/4 |
| 4,350,147 | 9/1982 | Sarrine .......................... 128/4 |
| 4,353,358 | 10/1982 | Emerson ....................... 128/4 |
| 4,425,919 | 1/1984 | Alston, Jr. et al. .......... 604/282 X |
| 4,576,772 | 3/1986 | Carpenter .................... 604/280 X |
| 4,580,551 | 4/1986 | Sigmund et al. .............. 128/4 |
| 4,726,355 | 2/1988 | Okada ............................ 128/4 |
| 4,773,395 | 9/1988 | Suzuki et al. ................. 128/4 |
| 4,805,596 | 2/1989 | Hatori ............................ 128/4 |
| 4,834,069 | 5/1989 | Umeda ........................... 128/4 |
| 4,850,351 | 7/1989 | Herman et al. ............. 128/303.1 |
| 4,873,965 | 10/1989 | Danieli .......................... 128/6 |
| 4,898,577 | 2/1990 | Badger et al. ................ 604/53 |
| 4,919,112 | 4/1990 | Siegmund ..................... 128/4 |
| 5,030,204 | 7/1991 | Badger et al. ................ 604/95 |
| 5,125,395 | 6/1992 | Adait ............................. 604/95 |
| 5,125,896 | 6/1992 | Hojeibane ..................... 604/95 |
| 5,167,221 | 12/1992 | Chikama ....................... 128/4 |
| 5,168,864 | 12/1992 | Shockey .................... 604/282 X |
| 5,176,660 | 1/1993 | Truckai ........................ 604/282 |

FOREIGN PATENT DOCUMENTS

| | | |
|---|---|---|
| 2130885A | 6/1984 | United Kingdom . |
| 8700442 | 1/1987 | World Int. Prop. O. .......... 604/280 |

OTHER PUBLICATIONS

"Diagnostic and Interventional Products for Radiology, Cardiology & Surgery," published by Cook, Inc., P.O. Box 489 Bloomington, IN 47402.

U.S. Patent Application for "131-Directional Miniscope," filed Jan. 9, 1992, Inventors: Donald Cohen and Alan DeLa Rama.

Primary Examiner—C. Fred Rosenbaum
Assistant Examiner—Frank Wilkens
Attorney, Agent, or Firm—John L. Rogitz

[57] ABSTRACT

An endoscope has a handle and a bendable tube extending distally away from the handle. The tube has a selectively deflectable distal segment. An activating wire is connected to the distal segment and to the handle, and the handle has a knob which can be turned to impart force to the wire and thereby cause the distal segment of the tube to deflect. The wire is held by a hypotube column support which is attached to the handle and to the deflectable distal segment, such that when the knob is turned, the column support transfers the force of the wire to the handle to prevent buckling of the bendable tube when the distal segment deflects.

19 Claims, 3 Drawing Sheets

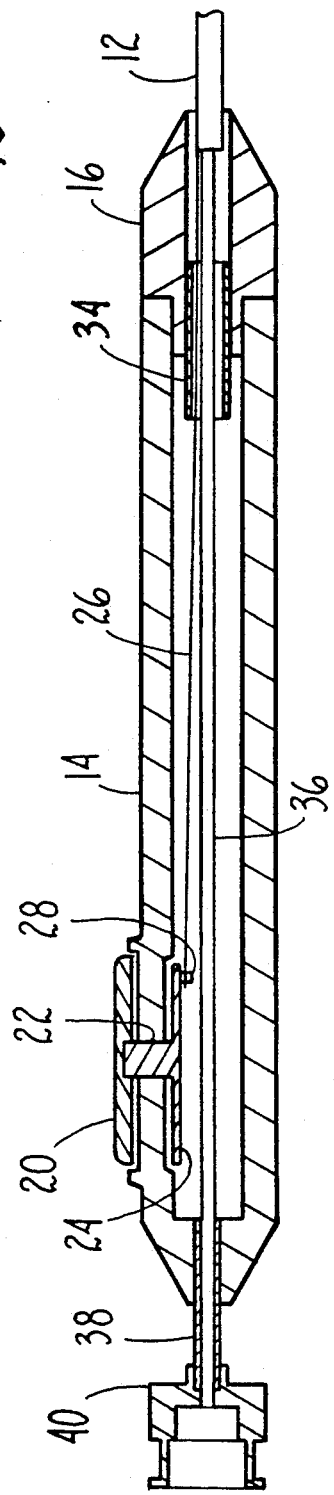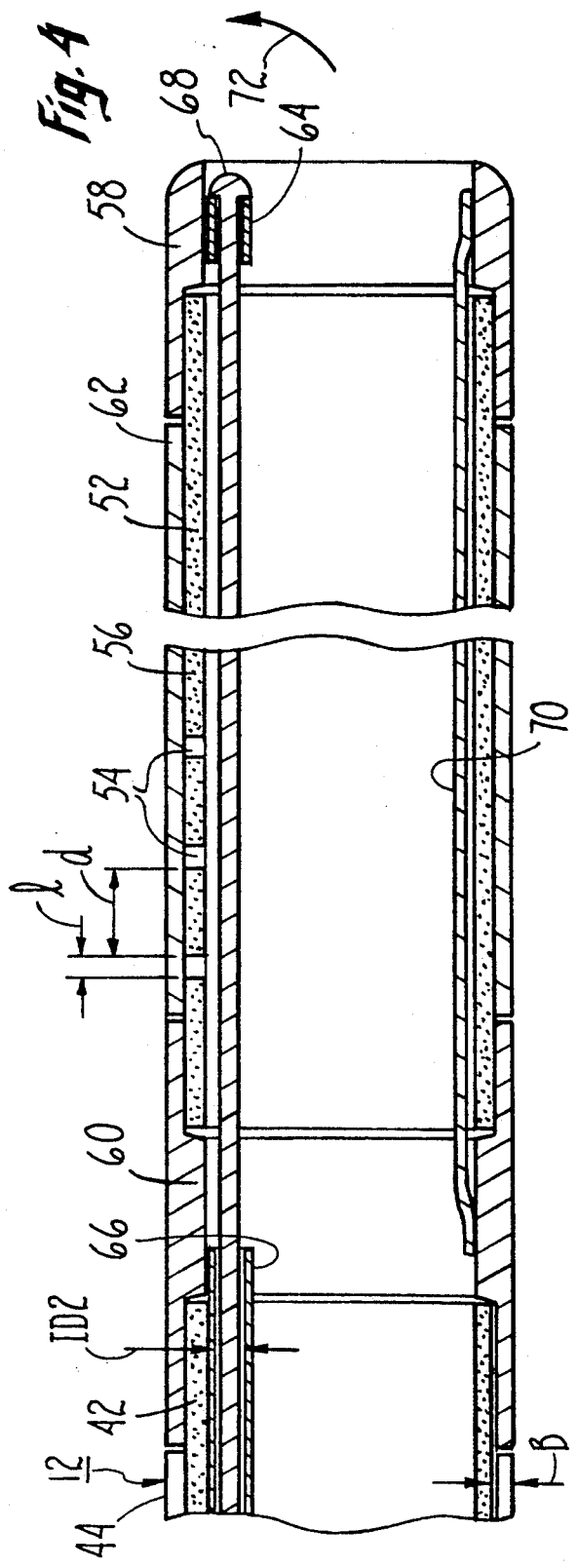

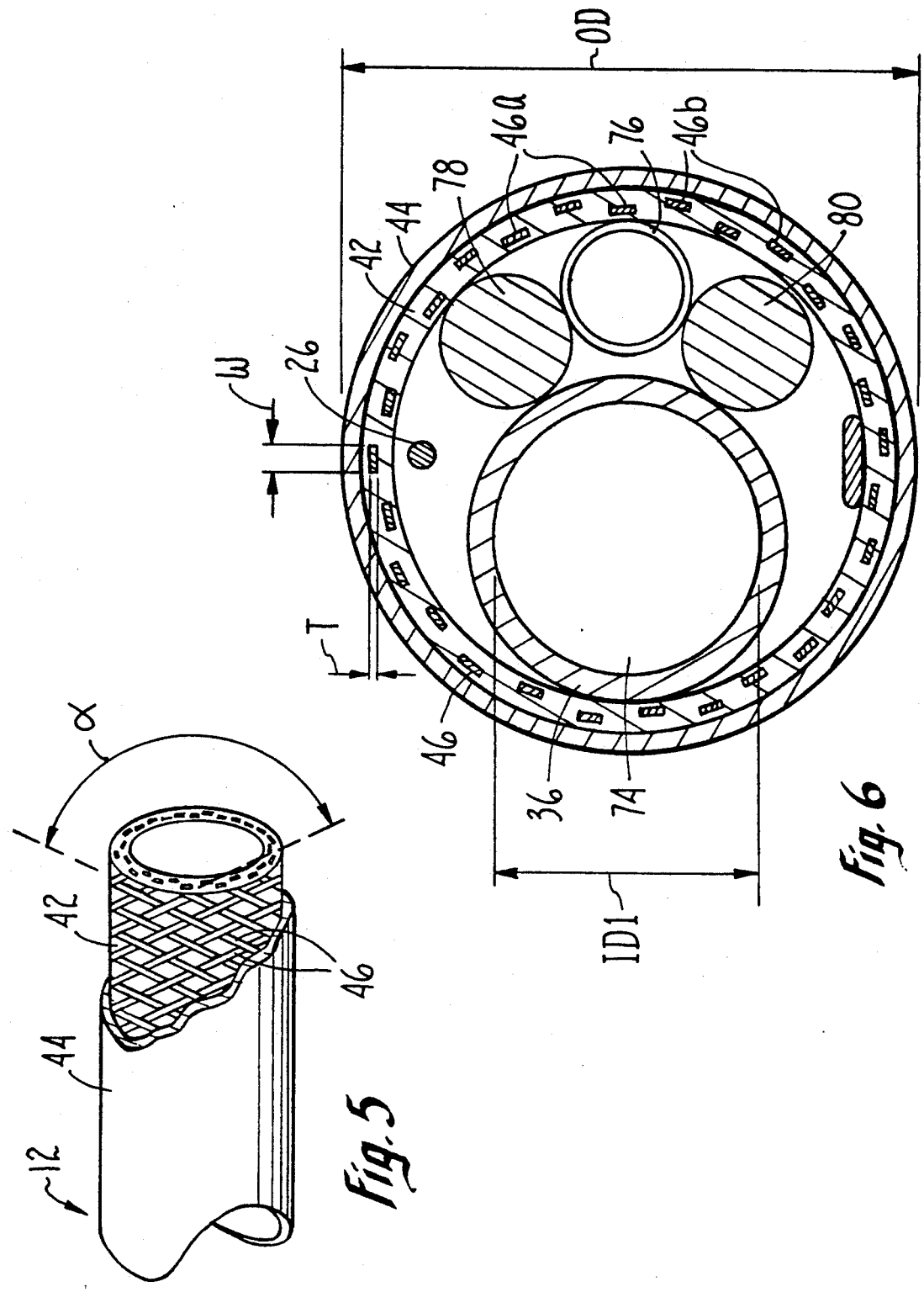

FLEXIBLE ENDOSCOPE WITH HYPOTUBE ACTIVATING WIRE SUPPORT

FIELD OF THE INVENTION

The present invention relates generally to endoscopes, and more particularly to flexible endoscopes which have deflecting tips.

BACKGROUND

Catheters are used for a large number of surgical procedures. For example, in many relatively new surgical techniques, e.g., endoscopic surgery, a small opening is made in the patient, and one or more catheters or cannulas are inserted into the opening to provide various working passageways through which small surgical instruments can be advanced into the patient to perform the particular procedure. To keep the opening as small as possible, it is desirable to minimize the diameter of the catheters.

Not surprisingly, it is sometimes advantageous that as the catheter is being positioned in the patient, the catheter be able to bend at predetermined locations, either to aid in advancing the catheter along a tortuous path or to avoid an obstructing object inside the patient. Simply pre-bending a catheter at a predetermined location on the catheter, however, can interfere with inserting the catheter along a straight-line path, and is therefore oftentimes undesirable.

Accordingly, past attempts have been made to make an entire catheter out of a flexible material. These devices sometimes provide a means for bending the catheter. One example of such a means is a manipulable wire connected to the catheter at the location where the bend is to occur. The catheter can be bent at the point of wire connection by pulling the wire.

Unfortunately, such devices are subject to buckling and do not always bend in proportion to the pulling force of the wire, making it difficult to reliably gauge the amount of pulling force necessary to bend the catheter an appropriate amount. Also, such catheters often lack structural strength to the extent that they can undesirably bend at unintended locations.

To overcome the structural strength problems mentioned above, catheters may be made of thin-walled strong and rigid material, such as steel. These catheters, however, cannot easily conform to the contours of a body vessel or duct. It is desirable for a catheter to conform to follow a body vessel or duct.

Accordingly, it is an object of the present invention to provide a catheter which can be bent at one or more predetermined location on the catheter. Another object of the present invention is to provide a small diameter, thin-walled bendable catheter that has a relatively high degree of structural strength. Further, it is an object of the present invention to provide a catheter which is easy to use and cost-effective to manufacture.

SUMMARY OF THE INVENTION

A flexible catheter has a bendable tube for conforming to the contour of a body vessel, and a selectively deflectable distal segment is connected to the tube coaxially with the tube. The distal segment can be selectively deflected without bending the flexible tube.

To provide a means for deflecting the distal segment, an activating wire which has a distal end is connected to the distal segment. Also, the activating wire has a proximal end, and the proximal end is manipulable to impart tension to the activating wire to thereby cause the distal segment to deflect. Further, a holder is provided for supporting the activating wire such that substantially no tension is imparted to the tube when the activating wire is under tension. Consequently, the distal segment can be selectively deflected without bending or buckling the bendable tube.

In a presently preferred embodiment, the deflectable distal segment has a distal end, and the holder includes an axially rigid fitting which is connected to the bendable tube and to the distal segment. Additionally, an axially rigid tip is attached to the distal end of the distal segment, and a hollow column support is disposed within the tube and is attached to the fitting.

To fixedly engage the activating wire with the tip (and, hence, the distal segment), a fitment is fixedly attached to the tip, and the distal end of the activating wire is attached to the fitment. Importantly, the activating wire extends through the column support in a slidable relationship therewith and does not contact the bendable tube. Consequently, when the activating wire is pulled in the proximal direction, the tension of the activating wire is transferred to the tip (and, hence, to the distal segment) to bend the distal segment, without bending the tube.

As intended by the present invention, the tube has a working channel lumen for establishing a working channel through which an endoscopic instrument can be advanced. Also, the tube has the capacity to accept an image fiber bundle and illumination fibers.

Preferably, the column support is a stainless steel tube such as hypodermic tubing. Alternatively, the column support can be a close clearance polymer tube integral to, or bonded along its entire length to, the flexible catheter tube.

A handle is positioned in a surrounding relationship to the tube to support the tube. The handle includes a deflection wheel which is rotatably engaged with the handle and which is connected to the activating wire. Accordingly, the deflection wheel can be rotated to pull the activating wire in the proximal direction and thereby bend the distal segment.

In another aspect of the present invention, a flexible catheter has a flexible tube and a bendable distal segment, and the distal segment has a distal end. An axially rigid fitting is connected to the flexible tube and to the bendable distal segment, and an axially rigid tip is attached to the distal end of the distal segment. Furthermore, a hollow column support is disposed within the tube and is attached to the fitting. Additionally, an activating wire is slidably disposed within the column support and is fixedly engaged with the tip. Consequently, the activating wire is manipulable to impart a pulling force on the tip to thereby bend the distal segment without substantially bending the flexible tube.

In yet another aspect of the present invention, a method for manipulating a surgical instrument in a body vessel is provided. According to the method of the present invention, a flexible catheter is provided, and a bendable distal segment is connected to the flexible catheter. Also, an activating wire is connected to the distal segment. The activating wire is supported such that when the activating wire is pulled in the proximal direction, the distal segment bends without substantially bending the flexible catheter.

The medical instrument is positioned in the catheter, and the catheter is advanced into the body vessel. Upon proper positioning of the catheter in the body vessel, the activating wire can be manipulated to selectively bend the distal segment.

The details of the present invention, both as to its construction and operation, can best be understood in reference to the accompanying drawings, in which like numerals refer to like parts, and which:

BRIEF DESCRIPTION OF THE DRAWINGS

FIG. 3 is a cross-sectional view of the flexible endoscope of the present invention, as seen along the line 3—3 in FIG. 1;

FIG. 4 is a cross-sectional view of the flexible endoscope of the present invention, as seen along the line 4—4 in FIG. 1, with the working channel tube and fiber optic tubes removed for clarity;

FIG. 5 is perspective view of the flexible tube of the endoscope of the present invention, with portions removed and portions broken away for clarity; and FIG. 6 is a cross-sectional view of the flexible endoscope of the present invention, as seen along the line 6—6 in FIG. 1.

DETAILED DESCRIPTION OF THE PREFERRED EMBODIMENT

Figure 1:
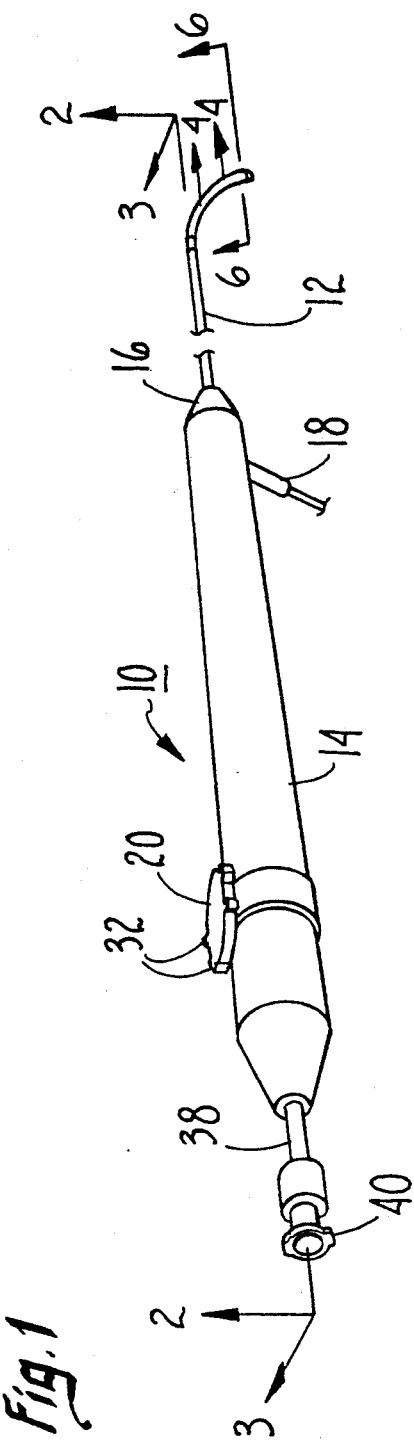
FIG. 1 is a perspective view of the flexible endoscope of the present invention, with portions broken away.

Referring initially to FIG. 1, a flexible endoscope is shown, generally designated 10. As shown in FIG. 1, the endoscope 10 includes a bendable tube 12 and a hollow handle 14, and the tube 12 extends distally outwardly from the handle 14. Preferably, the handle 14 is made of a strong, rigid, light-weight plastic or metal.

FIG. 1 also shows that the handle 14 has a hollow, distally-tapered frusto-conical nose piece 16. As shown in cross reference to FIGS. 1 and 2, the nose piece 16 includes a Y-fitting 18 which forms an obtuse angle with respect to the longitudinal axis of the endoscope 10. A light source and video display system (not shown) can be connected to the Y-fitting 18 for purposes to be subsequently disclosed.

Figure 2:
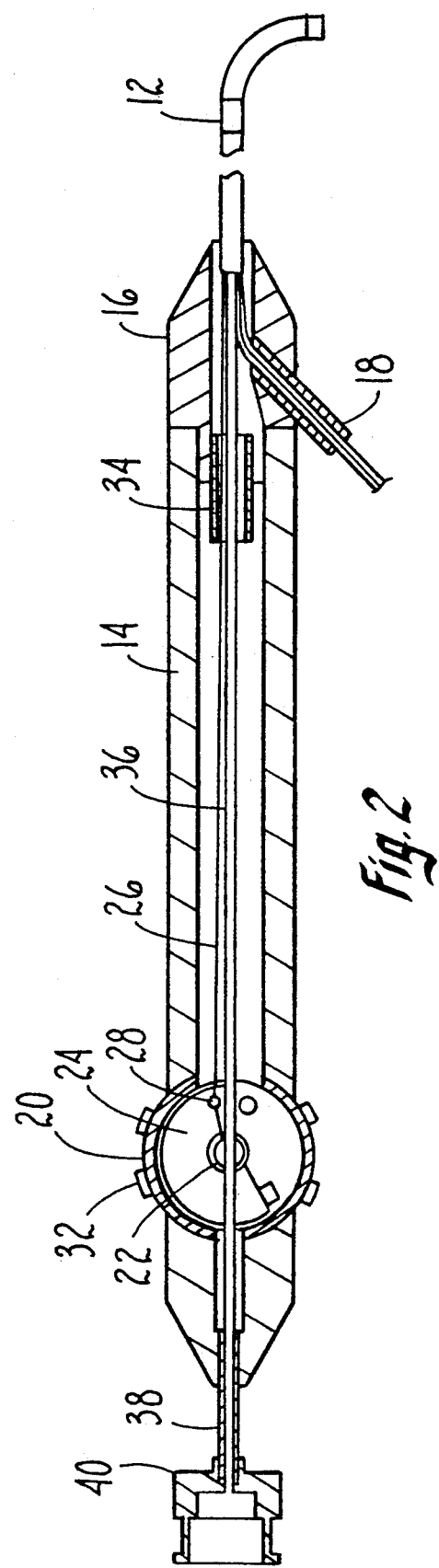
FIG. 2 is a cross-sectional view of the flexible endoscope of the present invention, as seen along the line 2—2 in FIG. 1.

In cross reference to FIGS. 1, 2, and 3, the handle 14 also includes a deflection wheel 20. As shown best in FIGS. 2 and 3, the deflection wheel 20 is rotatable mounted on the handle 14. More specifically, the deflection wheel 20 is connected to a deflection wheel shaft 22, and the deflection wheel shaft 22 is rotatably engaged with the handle 14. Also, the deflection wheel shaft 22 is attached to or formed integrally with a deflection wheel disk 24 which is disposed within the handle 14.

In accordance with the present invention, an activating wire 26 is attached to the deflection wheel shaft 22. The activating wire 26 has a diameter of about five thousandths of an inch (0.005") Additionally, the activating wire 26 is attached to a first wire anchor 28 attached to the deflection wheel 20. Accordingly, the deflection wheel 20 can be rotated, and the rotational motion of the deflection wheel 20 transferred to rotational motion of the deflection wheel disk 24 by the deflection wheel shaft 22, to thereby cause translational motion of the activating wire 26 for purposes to be disclosed below. As shown best in FIG. 2, to facilitate manipulating the deflection wheel 20, the deflection wheel 20 is formed with knurls 32.

In cross reference to FIGS. 2 and 3, in the presently preferred embodiment the nose piece 16 is not formed integrally with the handle 14, but instead is attached to the handle 14 by adhesive bonding and preferably by depositing a urethane adhesive between the nose piece 16 and handle 14. Indeed, a portion 31 of the nose piece 16 is hollow, and is filled with an epoxy material 33. A hollow nose piece tube 34 is bonded to the nose piece 16, and the nose piece tube 34 extends into the handle 14. Preferably, the nose piece tube 34 is made of a rigid material, such as stainless steel.

As shown, the nose piece tube 34 supports a working channel tube 36, and the working channel tube 36 extends into the endoscope tube 12. Preferably, the working channel tube 36 is made of a flexible material, e.g., polyurethane such as pellethane. The activating wire 26 is slidingly disposed in the hollow handle 14, and the wire 26 is juxtaposed with the working channel tube 36 and extends through the nose piece tube 34 into the endoscope tube 12.

Still referring to FIGS. 2 and 3, the working channel tube 36 extends through the handle 14 and is coaxial with the handle 14. FIG. 3 best shows that the deflection wheel disk 24 is positioned above the working channel tube 36 such that clearance exists between the disk 24 and working channel tube 36 to permit unimpeded manipulation of the deflection wheel 20.

FIGS. 2 and 3 further show that a handle tube 38 is bonded to the handle 14, and the working channel tube 36 extends through the handle tube 38. The handle tube 38 is in turn bonded to a luer fitting 40. An appropriate connecting device, such as a Touhy-Borst valve (not shown) made by Cook Incorporated, can be connected to the luer fitting 40. As is known in the art, a Touhy-Borst valve can include a Y-adapter, such that the Touhy-Borst valve can provide two passageways that extend into the working channel tube 36. Accordingly, a medical instrument (not shown) can be advanced axially through the Touhy-Borst valve and the luer fitting 40 and into the working channel tube 36 while irrigant 13 is infused through the side arm of the Y adapter.

FIGS. 4, 5, and 6 show further details of the endoscope tube 12. As shown in FIG. 4, the endoscope tube 12 includes a cylindrical braided polyimide body 42 which is covered by an Outer plastic sheath 44. The sheath 44 is made of polyethylene and has a thickness B of twenty five ten-thousandths of an inch (0.0025"), and the sheath 44 can be bonded to the polyimide body 42 at its ends or shrink fit around the polyimide body 42.

As intended by the present invention, the polyimide body 42 is reinforced with steel braids. More specifically, referring briefly to FIGS. 5 and 6, the polyimide body 42 has a plurality of steel ribbon braids 46 imbedded therein by means well known in the art, and the braids are positioned in the body 42 in a criss-crossing weave pattern.

As shown in FIGS. 5 and 6, the steel ribbon braids 46 are positioned in an open-braid configuration, i.e., no braid 46 contacts adjacent braids 46 that are positioned parallel to it. As shown best in FIG. 5, an angle $\alpha$ is formed between criss-crossing braids 46. In the preferred embodiment, the angle $\alpha$ is greater than 90 degrees and preferably greater than 115 degrees. Consequently, the endoscope tube 12 can accept a relatively small bend radius without kinking, i.e., a bend radius of one inch (1") or less. On the other hand, the angle $\alpha$ is preferably less than 130 degrees, so that the endoscope tube 12 can effectively transmit torque applied about the longitudinal axis of the tube 12.

As shown best in FIG. 6, each braid 46 has a width W that is equal to approximately five-thousandths of an inch (0.005"). Also each braid 46 has a thickness T that is approximately equal to seven ten-thousandths of an inch (0.0007"). FIG. 6 further shows that alternating braids 46 are staggered from each other, i.e., the braids 46a are closer to an inside surface 48 of the polyimide body 42 than are braids 46b.

The skilled artist will appreciate that the steel-braided polyimide body 42 can accordingly be bent about a transverse axis of the tube 12 in a relatively small bend radius. Also, the polyimide body 42 can effectively transmit torque that is applied about a longitudinal axis of the tube 12. Stated differently, rotational deflection due to torque which is applied to the polyimide body 42 about the longitudinal axis of the polyimide body 42 is substantially transferred along the length of the polyimide body 42. Alternatively, round wires (not shown) having a diameter of seven ten thousandths of an inch (0.0007") can be used in place of the steel ribbon braids 46, although this will change the effectiveness of torque transmission and kink resistance.

Referring back to FIG. 4, a selectively deflectable polyimide distal segment 52 is positioned coaxially with the polyimide body 42. As shown, the distal segment 52 has a plurality of notches 54 formed therein. The notches 54 are formed in a side surface 56 of the distal segment 52. Thus, the notches 54 do not extend completely through the distal segment 52. Each of the notches 54 has a length l of fifteen thousandths of an inch (0.015"), and the distance d between adjacent notches 54 is forty thousandths of an inch (0.040").

FIG. 4 further shows that the distal segment 52 is connected to a preferably stainless steel rigid tip 58, and the tip 58 is coaxial with the distal segment 52. Also, the distal segment 52 is connected with a cylindrical axially rigid fitting 60. Preferably, the fitting 60 is made of stainless steel. The notched distal segment 52 is bonded to the tip 58 and the fitting 60.

Still referring to FIG. 4, the fitting 60 is bonded to the polyimide body 42. Additionally, a distal sheath 62 is preferably shrink wrapped around the distal segment 52. FIG. 4 further shows that in the presently preferred embodiment, a cylindrical stainless steel fitment 64 is welded to the tip 58. The distal end 68 of the activating wire 26 is peened to prevent the distal end 68 from passing through the fitment 64.

As envisioned by the present invention, a hollow tubular column support 66 (FIG. 4) having an inside diameter ID2 of about six thousandths of an inch (0.006") is welded to the fitting 60, and the column support 66 extends through the polyimide body 42 and is bonded to the handle 14 outside the nose piece tube 34 (FIGS. 2 and 3). As shown, the activating wire 26 is slidably disposed in the column support 66. Thus, a clearance of preferably less than about two thousandths of an inch (0.002") or less is established between the wire 26 and column support 66. In the preferred embodiment, the column support 66 is a stainless steel hypotube. Alternatively, the column support 66 can be made of polyimide, or any other material which can bear the force of a tensioned activating wire 26 without buckling. Together, the tip 58, fitting 60, and column support 66 establish a holder for supporting the activating wire 26.

As intended by the present invention, the column support 66 reduces kinking and buckling of the polyimide tube 42 when the activating wire 26 is pulled in the proximal direction. When the column support 66 is made of a stainless steel hypotube, the force from an activating wire 26 under tension is borne by the hypotube itself.

FIG. 4 also shows that a metal, preferably stainless steel, stiffener 70 is welded to the tip 58 and to the fitting 60. It is to be understood that the combination of structure described above permits the distal segment 52 to be bent in a direction indicated by the arrow 72 when the activating wire 26 is pulled proximally. On the other hand, the distal segment 52 cannot be bent in a direction opposite the arrow 72. Thus, it is to be understood that the endoscope tube 12 shown in FIGS. 4, 5, and 6 is a unidirectionally bendable tube. Alternatively, a system of notches and stiffeners as described in U.S. patent application for an invention entitled "Flexible Tip Catheter", assigned to the same assignee as the present invention, Ser. No. 07/867,841, filed Apr. 13, 1992 incorporated herein by reference can be formed in April the distal segment 52 to enable the distal segment 52 to be bent bi-directionally or omni-directionally.

Now referring to FIG. 6, the detail of the endoscope tube 12 can be seen. Preferably, the outside diameter OD of the endoscope tube 12 is equal to approximately two and two-tenths millimeters (2.2 mm).

As shown in FIG. 6, the endoscope tube 12 includes a working channel 74 that is formed by the working channel tube 36. It is to be understood that an endoscopic instrument (not shown) can be advanced through the luer fitting 40, polyimide body 42, and distal segment 52 through the working channel 74, and the instrument can be advanced or retracted through the working channel 74. Preferably, the inside diameter ID1 of the working channel tube 36 is about one millimeter (1 mm).

FIG. 6 also shows that an image fiber tube 76 is positioned in the endoscope tube 12, and an optical image fiber and lens is disposed within the image fiber tube 76. The optical image fiber which is disposed in the fiber tube 76 extends through the endoscope tube 12 and into the Y-fitting 18 (FIG. 2). Thus, a video monitor (not shown) can be connected to the image fiber which is disposed in the image fiber tube 76 to display an image of an object located at the distal end of the image fiber tube 76.

Additionally, FIG. 6 shows that two optical illumination fibers 78, 80 are positioned in the endoscope tube 12. The optical illumination fibers 78, 80 extend through the endoscope tube 12 and into the Y-fitting 18, and can be connected to a source of illuminating light (not shown) for illuminating the object which is at the distal end of the image fiber tube 76. Preferably, the space between the illumination fiber tubes 78, 80, image fiber tube 76, and working channel tube 36 is filled with epoxy.

In the operation of the endoscope 10, reference is made to FIGS. 1, 2, and 3. First, a percutaneous incision is made in a patient (not shown). If desired, an entry cannula (not shown) can be inserted through the percutaneous incision and advanced to the site within the patient which is to be operated on.

Then, the endoscope tube 12 is advanced into the patient through the entry cannula until the distal end of the endoscope tube 12 has been positioned adjacent to the surgical site. An appropriate surgical instrument, e.g., a forceps, retractor, or scalpel, is advanced through the luer fitting 40, handle tube 38, through the handle 14, and the endoscope tube 12, to perform the particular surgical procedure.

More particularly, the endoscopic surgical instrument is advanced into the working channel tube 36 and is advanced to the distal end of the endoscope tube 12. Then, the surgical instrument can be advanced beyond the distal end of the endoscope tube 12 and the particular surgical procedure performed.

If desired, the endoscope tube 12 can be selectively bent to aid in advancing the tube 12 into the patient, or to aid in performing the particular surgical procedure with the endoscopic surgical instrument. More particularly, to bend the endoscope tube 12, the deflection wheel 20 is rotated. This pulls the activating wire 26 in the proximal direction. As the activating wire 26 is pulled in the proximal direction, the tension on the activating wire 26 is transferred to the fitment 64 and thus to the tip 58.

The entire endoscope tube 12, however, does not buckle or bend, because the column support 66 transfers the force of the activating wire 26 to the handle 14. Instead, only the distal segment 52 bends in a direction indicated by the arrow 72 (FIG. 4). When the deflection wheel 20 is released, the material bias of the distal segment 52 causes the distal segment 52 to straighten, i.e., to be co-linear with the rest of the endoscopic tube 12.

While the particular FLEXIBLE ENDOSCOPE WITH HYPOTUBE ACTIVATING WIRE SUPPORT as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is

1. A flexible catheter for an endoscope, comprising:
   a flexible tube;
   a bendable unitary distal segment having a plurality of notches formed therein, the distal segment having a distal end and defining a longitudinal axis;
   an elongated stiffener attached to the distal segment opposite the notches, the stiffener being positioned parallel to the longitudinal axis of the distal segment;
   an axially rigid fitting connected to the flexible tube and the bendable distal segment;
   an axially rigid tip attached to the distal end of the distal segment;
   a hollow column support disposed within the tube and attached to the fitting; and
   an activating wire slidably disposed within the column support and fixedly engaged with the tip, the activating wire being manipulable to impart a pulling force on the tip to thereby bend the distal segment without substantially bending the flexible tube.

2. The catheter of claim 1, further comprising an image fiber disposed in the tube.

3. The catheter of claim 2, wherein the tube is formed with a working channel lumen for establishing a working channel through which an endoscopic instrument can be advanced.

4. The catheter of claim 3, further comprising an illumination fiber disposed within the tube.

5. The catheter of claim 1, wherein the column support is a stainless steel hypotube.

6. The catheter of claim 5, further comprising a fitment fixedly attached to the tip, wherein the activating wire is attached to the fitment to thereby fixedly engage the activating wire with the tip.

7. The catheter of claim 1, wherein the column support is a polyamide tube.

8. The catheter of claim 1, wherein the flexible tube is a polyamide tube braided with steel ribbon.

9. The catheter of claim 1, further comprising a handle for supporting the flexible tube and a deflection wheel rotatable engaged with the handle and connected to the activating wire.

10. A flexible catheter, comprising:
    a bendable tube;
    a selectively deflectable unitary distal segment connected to the tube coaxially therewith, the distal segment having a wall formed with a plurality of notches and a stiffener attached to the wall opposite the notches;
    an activating wire having a distal end connected to the distal segment and a proximal end, the proximal end being manipulable to impart tension to the activating wire to thereby cause the distal segment to deflect; and
    a holder for supporting the activating wire such that substantially no force is imparted to the tube when the activating wire is under tension.

11. The catheter of claim 10, wherein the deflectable distal segment has a distal end, and the holder comprises:
    an axially rigid fitting connected to the bendable tube and the distal segment;
    an axially rigid tip attached to the distal end of the distal segment; and
    a hollow column support disposed within the tube and attached to the fitting.

12. The catheter of claim 11, wherein the tube has a working channel lumen for establishing a working channel through which an endoscopic instrument can be advanced, an image fiber lumen, and an illumination fibers.

13. The catheter of claim 12, wherein the column support is a stainless steel hypotube.

14. The catheter of claim 13, further comprising a fitment fixedly attached to the tip, wherein the activating wire is attached to the fitment to thereby fixedly engage the activating wire with the tip.

15. The catheter of claim 11, wherein the column support is a polyamide tube.

16. The catheter of claim 14, wherein the flexible tube is a polyamide tube braided with steel ribbon.

17. The catheter of claim 16, further comprising a handle for supporting the flexible tube and a deflection wheel rotatable engaged with the handle and connected to the activating wire.

18. A method for manipulating a surgical instrument in a body vessel, comprising the steps of:
    (a) providing a flexible catheter;
    (b) connecting a unitary bendable distal segment to the flexible catheter, the segment having a plurality of longitudinally-spaced notches and a stiffener positioned opposite the notches;

(c) connecting an activating wire to the distal segment;
(d) supporting the activating wire such that when the activating wire is pulled in the proximal direction, the distal segment bends without substantially bending the flexible catheter;
(e) positioning the medical instrument in the catheter;
(f) advancing the catheter into a body cavity; and
(g) manipulating the activating wire to selectively bend the distal segment.

19. A flexible catheter comprising:
a bendable tube;
a selectively deflectable unitary distal segment connected to the tube coaxially therewith, the segment being formed with a plurality of notches and having a stiffener disposed opposite the notches;
an activating wire having a distal end connected to the distal segment and a proximal end, the proximal end being manipulable to impart tension to the activating wire to thereby cause the distal segment to deflect; and
a holder for supporting the activating wire attached along its length to the bendable tube.

* * * * *